United States Patent [19]

Miwa et al.

[11] 4,219,359
[45] Aug. 26, 1980

[54] SINTERED BODY OF ZIRCONIA FOR OXYGEN CONCENTRATION SENSOR

[75] Inventors: Naoto Miwa, Tsushima; Masami Ouki, Nagoya; Katsuhiko Tanaka, Toyokawa; Masatosi Suzuki, Kariya, all of Japan

[73] Assignee: Nippondenso Co., Ltd., Kariya, Japan

[21] Appl. No.: 22,929

[22] Filed: Mar. 21, 1979

[30] Foreign Application Priority Data

Apr. 18, 1978 [JP] Japan .................................. 53-45710

[51] Int. Cl.$^2$ ...................... C04B 35/48; G01N 27/58
[52] U.S. Cl. .................................... 106/39.5; 106/57; 106/73.2; 204/195 S
[58] Field of Search .................... 106/39.5, 57, 73.2; 73/27 R; 338/34; 252/520, 521; 204/195 S

[56] References Cited

U.S. PATENT DOCUMENTS

| | | | |
|---|---|---|---|
| 3,268,349 | 8/1966 | Brixner | 106/39.5 |
| 3,432,314 | 3/1969 | Mazdiyasni et al. | 106/39.5 |
| 4,067,745 | 1/1978 | Garvie et al. | 106/57 |
| 4,125,407 | 11/1978 | Ueno | 106/57 |
| 4,152,234 | 5/1979 | Polliver | 204/195 S |

FOREIGN PATENT DOCUMENTS

| | | | |
|---|---|---|---|
| 1474029 | 3/1967 | France | 106/39.5 |
| 45-5503 | 2/1970 | Japan | 106/39.5 |

OTHER PUBLICATIONS

Duwez, P. et al., "Quantitative Analysis of Cubic and Monoclinic Zirconia by X-Ray Diffraction", J. Am. Cer. Soc. (1949), 32, pp. 180–183.

Kingery, W. D., "Oxygen Ion Mobility in Cubic $Zr_{0.85}Ca_{0.15}O_{1.85}$", J. Am. Cer. Soc. (1959), 42, pp. 393–398.

Takagi, H. et al., "Verfahren zur Herstellung sehr feiner Oxidpulver", Ber. Dt. Keram.S. GeR (1974), No. 8, pp. 234–235.

*Primary Examiner*—Helen M. McCarthy
*Attorney, Agent, or Firm*—Cushman, Darby & Cushman

[57] ABSTRACT

A sintered body of zirconia material for an oxygen concentration sensor exhibiting an electromotive force in accordance with the difference in the concentration of oxygen between a gas tested and a reference gas, consisting essentially of partially stabilized sintered zirconia and at least one additive selected from the group of yttrium oxide, calcium oxide and ytterbium oxide which zirconia has a cubic phase and a monoclinic phase existing in mingling relation. The ratio of the X-ray diffraction intensity of the surface ($11\bar{1}$) of the monoclinic phase to the X-ray diffraction intensity of the surface (111) of the cubic phase or the ratio $I(11\bar{1})/I(111)$ is in the range between 0.05 and 0.40, and the value of the X-ray diffraction intensity ratio caused by heating the sintered zirconia material to, and holding the same at, the temperature range between 200° and 300° C. minus the former ratio of the X-ray diffraction intensity is in the range between −0.05 and +0.10.

6 Claims, 1 Drawing Figure

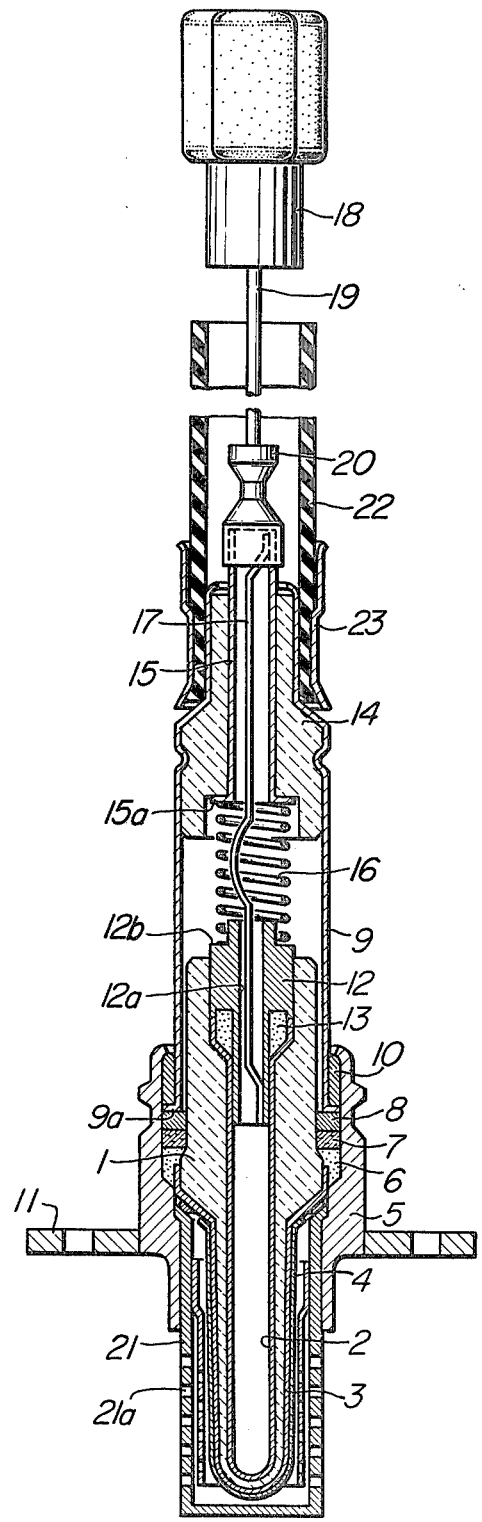

SINTERED BODY OF ZIRCONIA FOR OXYGEN CONCENTRATION SENSOR

BACKGROUND OF THE INVENTION

This invention relates to sintered bodies of zirconia for oxygen concentration sensors exhibiting an electromotive force in accordance with the difference in the concentration of oxygen between a gas tested and a reference gas, and more particularly to a sintered body of zirconia for an oxygen concentration sensor suitable for use in detecting the concentration of oxygen in waste gas of internal combustion engines.

This type of sintered body of zirconia has hitherto been produced by subjecting a divalent metallic oxide, such as calcium oxide, etc., or a trivalent metallic oxide, such as yttrium oxide (yttria), ytterbium oxide, etc., and zirconium oxide (zirconia) to heat treatment at high temperatures to cause them to form a solid solution, in order to produce oxygen ion conductivity. In this process, the amount of the divalent or trivalent metallic oxide added to zirconium oxide is selected such that the oxygen ion conductivity is maximized and the sintered body has a cubic crystal structure.

The results of experiments conducted by the inventors of the present invention show that although the sintered body of zirconia having a stabilized cubic crystal structure has a relatively high coefficient of thermal expansion and is not readily damaged by thermal impact when exposed to a gas atmosphere to be tested in which changes in temperature occur gradually, this sintered body of zirconia tends to produce excessively high thermal stress in its interior until it is finally damaged, when exposed to a gas atmosphere to be tested in which sudden changes in temperature occur as is the case with a waste gas of an internal combustion engine. In other words, it has been revealed that the sintered body of zirconia having a stabilized cubic crystal structure is low in thermal impact strength.

The inventors have conducted experiments in an effort to increase the thermal impact strength of sintered bodies of zirconia by solving this problem. As the result of the experiments, it has been ascertained that it is possible to increase the thermal impact strength of sintered zirconia of the stabilized cubic crystal structure by causing sintered zirconia of a monoclinic crystal structure to be present in the first-mentioned sintered zirconia in mingling relation in a sintered composite. In this context, the term "monoclinic" encompasses the monoclinic crystal system or a rhombic crystal system. When exposed to an atmosphere in which temperature rises, a sintered body of zirconia of the monoclinic crystal structure is altered through a tetragonal system into a cubic crystal structure, with an attendant change in volume. Therefore, if this sintered body of zirconia is used with an oxygen concentration sensor, it would be broken to pieces. This non-stabilized sintered body of zirconia of the monoclinic crystal structure has a low coefficient of thermal expansion, so that if it is caused to be present in a sintered body of zirconia of the cubic crystal structure in mingling relation, it would be possible to increase thermal impact strength of the sintered composite.

When exposed to a high temperature of about 800° C. which is prevailing in an waste gas of an internal combustion engine of an automotive vehicle, for example, the monoclinic crystal structure changes into a tetragonal crystal structure, which changes back into the monoclinic crystal structural when rapidly cooled. When this phenomenon occurs, a change occurs in the volume of the monoclinic crystal structural portions or gaps are formed in the grain boundary of the monoclinic crystal structural portions. It is believed that although cracks are formed in the cubic crystal structural portions when the sintered body is rapidly cooled, the gaps formed in the grain boundary of the monoclinic crystal structural portions would inhibit the occurrence of the bridging between the cracks formed in discrete cubic crystal structural portions, if the sintered body of zirconia of the monoclinic crystal structure were present in mingling relation to the sintered body of zirconia of the cubic crystal structure with the result that the cracks would be prevented from increasing their size. It is also believed that the monoclinic crystal structural portions would not readily develop cracks because of their very low coefficient of thermal expansion. It would seem that under these circumstances the sintered body of zirconia has its thermal impact strength increased and does not readily develop cracks. It is known that when a partially stabilized sintered body of zirconia including a monoclinic crystal system and a cubic crystal system existing in mingling relation is cooled from a high temperature level to a low temperature level, the ratio of monoclinic crystal structure increases. However, it has recently been ascertained as a result of research that portions of the cubic crystal structure remain the same phase as that in high temperature state and do not change into the monoclinic phase, when cooled. Even if allowed to stand at room temperature, the majority of the partially stabilized sintered bodies of zirconia do not show changes in the cubic phase and the monoclinic phase so far as X-ray diffraction is concerned. However, experiments conducted repeatedly by the present inventors have revealed that prolonged holding of this type of sintered body of zirconia at the range between 200° and 300° C., particularly at 200° C., or subjecting of this type of sintered body of zirconia to repeated changes in temperature in the aforesaid temperature range causes a change to occur with respect to the X-ray diffraction intensity ratio of the monoclinic crystal structure and the cubic crystal structure, and causes damage to the sintered body, if the change is great.

SUMMARY OF THE INVENTION

This invention has as its object the provision of a sintered body of zirconia suitable for use with an oxygen concentration sensor, which is high in thermal impact strength and has a long service life.

The characteristic features of the present invention are that the sintered body of zirconia is formed of partially stabilized sintered zirconia material including a cubic phase and a monoclinic phase existing in mingling relation, that the ratio of the X-ray diffraction intensity of the surface (11$\bar{1}$) of the monoclinic phase to the X-ray diffraction intensity of the surface (111) of the cubic phase or the ratio $I(11\bar{1})/I(111)$ is in the range between 0.05 and 0.40, and that changes in the value of the X-ray diffraction intensity ratio caused by heating the sintered body of zirconia to the temperature range between 200° and 300° C. (that is, the X-ray diffraction intensity ratio after heating minus the X-ray diffraction intensity ratio before heating) are in the range between −0.05 and +0.10. By virtue of these features, the sintered body of zirconia resists the formation of cracks when exposed to a gas to be tested which shows marked changes in temperature. Prolonged holding of the sintered body of zirconia in a gas to be tested which is in the low temperature range between 200° and 300° C. does not readily cause crack formation in the body of sintered zirconia.

Other and additonal objects, features and advantages will become apparent from the description set forth hereinafter when considered in conjunction with the accompanying drawing.

BRIEF DESCRIPTION OF THE DRAWING

The drawing is a fragmentary sectional view of an oxygen concentration sensor in which the sintered body of zirconia according to the present invention is incorporated.

DESCRIPTION OF THE EMBODIMENTS

The invention will now be described by referring to the embodiments. After adjusting the grain size of commercially available zirconia ($ZrO_2$) and at least one commercially available additive selected from the group consisting of yttria ($Y_2O_3$), calcium oxide and ytterbium oxide to a level of 1 to 5$\mu$, the powder materials are made to have predetermined mol% shown in Table 1, and was mixed and ground for 20 to 80 hours in a pot mill to reduce the grain size to below 1$\mu$. Zirconia containing, as solid solution, yttria etc. of a larger mol% than the predetermined mol% and zirconia containing, as solid solution, yttria etc. of a smaller mol% than the predetermined mol% may be mixed with each other to bring the mol% of the mixture to the predetermined mol% level shown in Table 1. In the mixture were added water and a binder, such as polyvinyl alcohol, in an amount of 0.2% with respect to the mixture, and then the granulation thereof was effected by using a known spray drier. The granulated mixture was shaped into a compact body by means of a known rubber press. The compact body was formed by a grinder into a tubular body open at one end and closed at the other end, which had an inner diameter of 4 mm, an outer diameter of 8 mm and a length of 47 mm. The tubular body was sintered at a temperature selected from the range between 1450° and 1800° C. By selecting a sintering temperature from this range, either stabilized or partially stabilized sintered bodies of zirconia shown in FIG. 1 were alternatively produced.

The sintered bodies of zirconia produced by the method described above were tested with respect to thermal impact strength by steps described hereinafter. A heat sensing part of a chromel-alumel thermocouple was placed inside the closed end of each sintered body of zirconia, and the thermocouple was connected to a recorder so that the temperatures might be read out with the lapse of time. Thus it was possible to calculate the rate of an increase or reduction in temperature (°C./sec) per unit time (second). Then the sintered body of zirconia was positioned relative to a burner using a gas-air mixture of city gas and compressed air in such a manner that the flame formed in the burner contacted a portion of the sintered body which portion is defined by a length from the closed end up to about 15 mm along its length. The burner was ignited after the sintered body and the burner were positioned as aforesaid, and the temperatures of the sintered body of zirconia were recorded by means of the recorder, to determine changes in temperature. After this thermal impact test was finished, the cooled sintered body of zirconia was subjected to a color test in which the sintered body was fuchsine-dyed to determine the presence or absence of cracks therein. The rates of changes in temperature at which cracks were formed in various sintered bodies were obtained, and it has been concluded that the higher the rate of change in temperature until the crack forming temperature is reached, the higher is the thermal impact strength of a sintered body. Also, the sintered bodies of zirconia were crushed and by use of X-ray diffraction means to obtain the ratio of the X-ray diffraction intensity of the surface (11$\bar{1}$) of the monoclinic phase to the X-ray diffraction intensity of the surface (111) of the cubic phase, i.e., the ratio $I(11\bar{1})/I(111)$. Then the ratio $I(11\bar{1})/I(111)$ was obtained again after the sintered bodies were held at 200° C. for 1,000 hours, and the surface of each sintered body was examined with electron microscope (about 1000 magnification) to determine the presence or absence of cracks. The results of these tests are shown in Table 1.

Table 1

| | | | Initial value | | Value after heating at 200° C. for 1000 hrs. | | | |
|---|---|---|---|---|---|---|---|---|
| Exp. | Mol% of Zirconia | Mol% of additions for stabilization | $I(11\bar{1})$ Monoclinic $I(111)$ Cubic | Rate of Temp. change at which Cracks occur (°C./sec) | $I(11\bar{1})$ Monoclinic $I(111)$ Cubic | Presence or absence of cracks observed by electron microscope | Value of change from initial value | Note |
| 1 | 90 | $Y_2O_3$ 10 | 0 | 40 | 0 | o | | Stabilized Zirconia |
| 2 | 91 | $Y_2O_3$ 9 | 0 | 40 | 0 | o | | " |
| 3 | 93 | $Y_2O_3$ 7 | 0 | 40 | 0 | o | | " |
| 4 | 93 | $Y_2O_3$ 7 | 0.01 | 40 | 0.01 | o | 0 | Partially stabilized Zirconia |
| 5 | 93 | $Y_2O_3$ 7 | 0.05 | 45 | 0.05 | o | 0 | " |
| 6 | 94 | $Y_2O_3$ 6 | 0.05 | 45 | 0.07 | o | 0.02 | " |
| 7 | 94 | $Y_2O_3$ 6 | 0.10 | 50 | 0.12 | o | 0.02 | " |
| 8 | 95 | $Y_2O_3$ 5 | 0.01 | 40 | 0.10 | x | 0.09 | " |
| 9 | 95 | $Y_2O_3$ 5 | 0.06 | 45 | 0.08 | o | 0.02 | " |
| 10 | 95 | $Y_2O_3$ 5 | 0.10 | 60 | 0.12 | o | 0.02 | " |
| 11 | 95 | $Y_2O_3$ 5 | 0.20 | 60 | 0.20 | o | 0 | " |
| 12 | 95 | $Y_2O_3$ 5 | 0.30 | 60 | 0.25 | o | −0.05 | " |
| 13 | 96 | $Y_2O_3$ 4 | 0.02 | 40 | 0.20 | x | 0.18 | " |
| 14 | 96 | $Y_2O_3$ 4 | 0.05 | 45 | 0.20 | x | 0.15 | " |
| 15 | 96 | $Y_2O_3$ 4 | 0.10 | 60 | 0.22 | x | 0.12 | " |
| 16 | 96 | $Y_2O_3$ 4 | 0.15 | 60 | 0.22 | o | 0.07 | " |
| 17 | 96 | $Y_2O_3$ 4 | 0.25 | 60 | 0.30 | o | 0.05 | " |
| 18 | 96 | $Y_2O_3$ 4 | 0.40 | 60 | 0.35 | o | −0.05 | " |
| 19 | 96 | $Y_2O_3$ 4 | 0.50 | 60 | 0.30 | x | −0.202 | " |
| 20 | 96 | $Y_2O_3$ 4 | 0.70 | 60 | 0.30 | x | −0.40 | " |

Table 1-continued

| | | | Initial value | | Value after heating at 200° C. for 1000 hrs. | | | |
|---|---|---|---|---|---|---|---|---|
| Exp. | Mol% of Zirconia | Mol% of additions for stabilization | I(111) Monoclinic I(111) Cubic | Rate of Temp. change at which Cracks occur (°C./sec) | I(11̄1) Monoclinic I(111) Cubic | Presence or absence of cracks observed by electron microscope | Value of change from initial value | Note |
| 21 | 97 | $Y_2O_3$ 3 | 0.20 | 60 | 0.40 | x | 0.20 | " |
| 22 | 95.5 | $Y_2O_3$ 4.5 | 0.25 | 60 | 0.21 | o | −0.04 | " |
| 23 | 95.5 | $Y_2O_3$ 4.5 | 0.12 | 60 | 0.06 | x | −0.06 | " |
| 24 | 95.5 | $Y_2O_3$ 4.5 | 0.34 | 60 | 0.27 | x | −0.07 | " |
| 25 | 95.5 | $Y_2O_3$ 4.5 | 0.08 | 55 | 0.18 | o | 0.10 | " |
| 26 | 93 | $Y_2O_3$ 4 CaO 3 | 0.15 | 50 | 0.20 | o | 0.05 | " |
| 27 | 90 | CaO 10 | 0.10 | 45 | 0.14 | o | 0.04 | " |
| 28 | 95 | $Y_2O_3$ 3 $Yb_2O_3$ 2 | 0.15 | 50 | 0.18 | o | 0.03 | " |
| 29 | 95 | $Y_2O_3$ 2 $Yb_2O_3$ 3 | 0.10 | 50 | 0.14 | o | 0.04 | " |
| 30 | 95 | $Y_2O_3$ 5 | 0.045 | 40 | 0.056 | x | +0.11 | " |

Note:
o No Cracks
x Cracks present

Experiment Nos. 1 to 3 shown in Table 1 refer to stabilized sintered bodies of zirconia of the prior art including the cubic phase only. As can be seen in Table 1, experiment Nos. 4, 8, 13 and 30 have the same rate of change to the crack forming temperature as the sintered bodies of zirconia of the prior art and are low in thermal impact strength. On the other hand, it will be seen that the sintered bodies of other experiment numbers have higher thermal impact strength than the sintered bodies of zirconia of the prior art. When put to service for an extended period, the sintered bodies of Nos. 19 and 20 have been found to suffer damage, due to a large value of X-ray diffraction intensity ratio and a large proportion of cubic phase. As can be seen in Table 1, the sintered bodies of zirconia which have a great change in the X-ray diffraction intensity ratio after being heated at 200° C. for 1,000 hours, such as those of experiment Nos. 14, 15, 21, 23 and 24, for example, show crack formation on the surface. As aforesaid, prolonged holding of a partially stabilized sintered body of zirconia at 200° to 300° C. causes a change to occur in the X-ray diffraction intensity ratio, and when this change is great, cracks are formed in the partially stabilized sintered body of zirconia. It has been found that this tendency is strongest when the sintered body is held at 200° C. for a prolonged period of time. Therefore, it will be seen that the sintered bodies of zirconia which do not cause cracks when held at 200° C. for a prolonged period of time do not cause cracks when held at 300° C. for a prolonged period of time.

The inventors have studied the results of tests shown in Table 1 to determine the characteristic values of a sintered body of zirconia which has higher thermal impact strength than sintered bodies of zirconia of the prior art and does not cause cracks even if held at 200° to 300° C. for a prolonged period of time. It has been revealed that these characteristic values are in the range between 0.05 and 0.40 of the ratio I(11̄1)/I(111), that is, the ratio of the X-ray diffraction intensity of the surface (11̄1) of the monoclinic phase to the X-ray diffraction intensity of the surface (111) of the cubic phase while the change of value with respect to the above-mentioned X-ray diffraction intensity ratio after maintaining the sintered body at a temperature of 200° to 300° C. is in the range between −0.05 and 0.10.

One example of the oxygen concentration detecting element incorporating therein the sintered body of zirconia according to the present invention will now be described by referring to the drawing. The numeral 1 designates the oxygen concentration detecting element formed of the sintered body of zirconia according to the present invention containing 95 mol% of zirconia and 5 mol% of yttria forming a solid solution with each other. The element 1 is in the form of a tube composed of a major diameter portion and a minor diameter portion which is open at one end and closed at the other end. The element 1 is formed on its inner and outer surfaces with first and second electrode layers 2 and 3 respectively, which are porous layers formed of platinum having a catalytic action and are provided by chemical plating, vaporization deposition in vacua, paste baking, and etc. The second electrode layer 3 extends from the closed end area of the outer surface of the element 1 which is exposed to waste gas to the open end area thereof which is not exposed to waste gas. The portion of the surface of the second electrode layer 3 which is exposed to waste gas is provided with a protective layer 4 of heat resisting porous material, such as magnesia, alumina spinel ($MgAl_2O_4$) or other metallic oxide. A housing 5 of the cylindrical shape formed of heat resisting metal, such as 18 chromium stainless steel, encloses the oxygen concentration detecting element 1. A conductive layer of graphite powder 6, an absestos ring 7 and a conductive metallic ring 8 are arranged between the element 1 and the housing 5. One end portion of a protective tubular member 9 formed of conductive heat resisting metal, such as stainless steel, extends between the housing 5 and the element 1 and is formed with a flange 9a at the end which supports thereon a spacer ring 10 formed of 18 chrominum stainles steel or other conductive material. The housing is pinched tightly at the upper portion thereof to secure the same to the oxygen concentration detecting element 1 and at the same time to secure one end of the protective tubular member to the element. The housing 5 has secured thereto a flange 11 for securing the element to an exhaust conduit, not shown. The portion of the surface of the element 1 which is not exposed to waste gas is covered with one end portion of the protective tubular member 9 as aforesaid. A stem 12 formed of conductive metal, such as stainless steel, and having an axial bore 12a therein is fitted in the open end of the element 1 while secured to the inner surface of the element 1 through a conductive layer of graphite powder 13. An insulator 14 formed of alumina or other material is fitted in the other end portion of the protective tubular member 9 and held in place by pinching the tubular member 9. A hollow tube 15 formed of conductive metal, such as stainless steel, and formed with a flange 15a is inserted in the central portion of the insulator 14, and a spring 16 is mounted between the flange 15a and a shoulder 12a formed in the stem 12. The stem 12 is in pressure contact with the oxygen concentration detecting element 1 by the set load of the spring 16, so that the stem is held securely on the element 1. A stainless wire 17 is joined by welding at one end thereof to the wall of the bore 12a of the stem 12 and is joined by welding at the other end thereof to the inner upper portion of the tube 15. A lead 19 of a connector 18 is secured, through a terminal 20, to the end of the hollow tube 15 opposite to the flange 15a, by pinching. A double type protective tube 21 provided with many small apertures 21a is secured to the lower end of the housing 5 in such a manner as to cover the portion of the outer surface of the oxygen concentration detecting element 1 which is exposed to waste gas. The first electrode layer 2 of the element 1 is electrically connected to the lead 19 through the conductive layer of graphite powder 13, stem 12, stainless steel wire 17 and tube 15, or through the spring 19 midway. The second electrode layer 3 of the element 1 is electrically connected to the housing 5 through the conductive layer of graphite powder 6 and conductive ring 6. 22 designates a heat resisting rubber tube fitting over the protective tubular member 9 through a collar 23.

The embodiment described hereinabove can be modified in various ways as follows.

(1) In the aforesaid embodiment, the oxygen concentration detecting element 1 is formed of a partially stabilized sintered body of zirconia produced by adjusting the mol% of zirconia, mol% of the additive for stabilization, grain size of the material and sintering temperature of the composite. The invention is not limited to this process of production, and the partially stabilized sintered body of zirconia can be produced by adjusting the rate of mixing of stabilized zirconia and non-stabilized zirconia. The partially stabilized sintered body of zirconia can be produced also by adding sintering promoting material, such as kaolin, talc, etc., to zirconia and an additive for stabilization. The partially stabilized sintered body of zirconia can be produced by altering the sintering atmosphere (oxydizing or reducing) or by aging.

(2) In the aforesaid embodiment, yttria is used as a stabilizing additive. However, the object of the invention can be accomplished by using one or a plurality of divalent or trivalent stabiling agents, such as calcium oxide, scandium oxide, ytterbium oxide, magnasium oxide, and etc., either singly or in combination.

(3) The sintered body of zirconia according to the present invention is not limited, in usage to the detection of the concentration of oxygen in waste gas of internal combustion engines of automotive vehicles, and can be used in many other usage.

As aforesaid, according to the present invention, there is provided a sintered body of zirconia for an oxygen concentration sensor, formed of partially stabilized sintered material including a cubic phase and a monoclinic phase existing in mingling relation, wherein the ratio of the X-ray diffraction intensity of the surface $(11\bar{1})$ of the monoclinic phase to the X-ray diffraction intensity of the surface $(111)$ of the cubic phase, i.e., the X-ray diffraction intensity ratio $I(11\bar{1})/I(111)$ is in the range between 0.05 and 0.40, and changes in the value of the X-ray diffraction intensity ratio caused by heating the sintered zirconia material to, and holding the same at, the range between 200° and 300° C. are in the range between $-0.05$ and $+0.10$. By virtue of the aforesaid features, the sintered body of zirconia according to the present invention has higher thermal impact strength, resists the occurence of cracks caused by thermal impact when exposed to a gas to be tested which gas shows markedly abrupt rise and fall in temperature, and resists the occurence of cracks when held at a low temperature of from 200° to 300° C. for a prolonged period of time or repeatedly in such conditions, than stabilized sintered bodies of zirconia of the prior art. Thus the sintered body of zirconia according to the present invention has high thermal impact strength and is highly durable, so that it is suitable for use with an oxygen concentration sensor.

What is claimed is:

1. A sintered body of zirconium oxide material for an oxygen concentration sensor exhibiting an electromotive force in accordance with the difference in the concentration of oxygen between a gas to be tested and a reference gas, consisting essentially of partially stabilized zirconium oxide and at least one additive selected from the group of yttrium oxide, calcium oxide and ytterbium oxide which zirconium oxide has cubic and monoclinic phases both existing in mingling relation, said additive being solid-soluted in zirconium oxide, wherein the ratio of the X-ray diffraction intensity of the surface $(11\bar{1})$ of the monoclinic phase to the X-ray diffraction intensity of the surface $(111)$ of the cubic phase, or the X-ray diffraction intensity ratio $I(11\bar{1})/I(111)$, is in the range between 0.05 and 0.40, and the changes in value of the X-ray diffraction intensity ratio $I(111)/I(111)$ caused by heating and holding the partially stabilized sintered material of zirconium oxide at the range between 200° and 300° C. minus the initial X-ray diffraction intensity ratio $I(111)/I(111)$ obtained before heating and holding the partially stabilized sintered material of zirconium oxide at the range between 200° and 300° C. are in the range between $-0.05$ and $+0.10$.

2. A sintered body of zirconium oxide material as set forth in claim 1, wherein said sintered body of zirconium oxide material contains 4 to 7 mol% of yttrium oxide as an additive for partially stabilizing the zirconium oxide.

3. A sintered body of zirconium oxide material as set forth in claim 1, wherein said sintered body of zirconium oxide material contains 10 mol% of calcium oxide.

4. A sintered body of zirconium oxide material as set forth in claim 1, wherein said sintered body of zirconium oxide material contains 3 mol% of yttrium oxide and 2 mol% of ytterbium.

5. A sintered body of zirconium oxide material as set forth in claim 1, wherein said sintered body of zirconium oxide contains 2 mol% of yttrium oxide and 3 mol% of ytterbium.

6. A sintered body of zirconium oxide material as set forth in claim 1, wherein said sintered body of zirconium oxide material contains 4 mol% of yttrium oxide and 3 mol% of calcium oxide.

* * * * *